United States Patent
Li et al.

(10) Patent No.: US 10,975,366 B2
(45) Date of Patent: Apr. 13, 2021

(54) METHOD FOR EFFICIENTLY EXPRESSING PULLULANASE IN BACILLUS SUBTILIS AND RECOMBINANT BACILLUS SUBTILIS

(71) Applicant: GUANGDONG VTR BIO-TECH CO., LTD, Guangdong (CN)

(72) Inventors: Yangyuan Li, Guangdong (CN); Jianrong Wang, Guangdong (CN); Ling Yang, Guangdong (CN); Man Qu, Guangdong (CN); Lizhi Chen, Guangdong (CN); Jiale Huang, Guangdong (CN)

(73) Assignee: GUANGDONG VTR BIO-TECH CO., LTD, Guangdong (CN)

( * ) Notice: Subject to any disclaimer, the term of this patent is extended or adjusted under 35 U.S.C. 154(b) by 0 days.

(21) Appl. No.: 16/476,878

(22) PCT Filed: Oct. 24, 2017

(86) PCT No.: PCT/CN2017/107476
§ 371 (c)(1),
(2) Date: Jul. 10, 2019

(87) PCT Pub. No.: WO2018/129980
PCT Pub. Date: Jul. 19, 2018

(65) Prior Publication Data
US 2020/0140839 A1    May 7, 2020

(30) Foreign Application Priority Data
Jan. 16, 2017   (CN) .......................... 201700032183.9

(51) Int. Cl.
*C12N 9/54*    (2006.01)
*C12N 9/44*    (2006.01)

(52) U.S. Cl.
CPC ............. *C12N 9/54* (2013.01); *C12N 9/2457* (2013.01); *C12Y 302/01041* (2013.01)

(58) Field of Classification Search
CPC . C12N 9/54; C12N 9/2457; C12Y 302/01041
See application file for complete search history.

(56) References Cited

U.S. PATENT DOCUMENTS

| | | | | |
|---|---|---|---|---|
| 5,294,542 A * | 3/1994 | Sloma | ...... | C12N 9/54 435/222 |
| 5,698,415 A * | 12/1997 | Jørgensen | ...... | C12N 9/1074 435/69.1 |
| 5,955,310 A * | 9/1999 | Widner | ...... | C12N 15/75 435/183 |
| 6,287,826 B1 * | 9/2001 | Norman | ...... | C12N 9/2417 435/98 |
| 10,138,268 B2 * | 11/2018 | Quaedflieg | ...... | C07K 1/36 |
| 10,287,592 B2 * | 5/2019 | Van Rij | ...... | C12P 21/00 |
| 10,400,228 B2 * | 9/2019 | Fan | ...... | C12P 19/02 |

OTHER PUBLICATIONS

Kawamura et al., Construction of Bacillus subtilis double mutatnt deficient in extracellular alkaline and neutral proteases. J. Bacteriol., 1984, vol. 160(1): 442-444. (Year: 1984).*

Moran et al., Nucleotide seqeunces that signal the initiation of transcription and translation in Bacillus subtilis. Mol Gen Genet., 1982, vol. 186: 339-346. (Year: 1982).*

Widner et al., Development of marker-free strains of Bacillus subtilis capable of secreting high levels of industrial enzymes. J. Ind Microbiol Biotechnol., 2000, vol. 25: 204-212. (Year: 2000).*

Waldeck et al., Isolation and molecular characterization of chitinase-deficient Bacillus licheniformis strains capable of deproteinization of shrimp shell waste to obtain highly viscous chitin. Appl. Environ. Microbiol., 2006, vol. 72(12): 7879-7885 (Year: 2006).*

* cited by examiner

*Primary Examiner* — Ganapathirama Raghu
(74) *Attorney, Agent, or Firm* — Patshegen IP LLC; Moshe Pinchas (57) ABSTRACT

The present invention relates to the field of genetic engineering, particularly to a method for efficiently expressing pullulanase in *Bacillus subtilis* and recombinant *Bacillus subtilis*. said method includes steps of constructing modified *Bacillus subtilis* strain with deletion of alkaline protease gene and neutral protease gene, constructing expression vector including an optimized combination of promoter and signal peptide and pullulanase gene, and transforming said modified *Bacillus subtilis* strain with by said expression vector. A series of combinations of promoter and signal peptide are optimized to obtain the combination for efficiently expressing pullulanase, provide an industrial application basis.

2 Claims, 2 Drawing Sheets
Specification includes a Sequence Listing.

METHOD FOR EFFICIENTLY EXPRESSING PULLULANASE IN BACILLUS SUBTILIS AND RECOMBINANT BACILLUS SUBTILIS

FIELD OF THE INVENTION

The present invention relates to the field of genetic engineering, particularly to a method for efficiently expressing pullulanase in *Bacillus subtilis* and recombinant *Bacillus subtilis*.

BACKGROUND OF THE INVENTION

Starch is composed of 15%-25% of amylose consisting of linear glucose by α-1,4 glycoside bonds and 75%-85% of amylopectin with the branches formed by several oligosaccharides binding to the main chain by means of α-1,6 glycoside bonds. Because of the special structure of starch, there is a need of synergetic interaction of several enzymes to hydrolyze starch with high molecular weight into oligosaccharides, disaccharides and monosaccharides. Pullulanase can specifically hydrolize α-1,6 glycoside bonds of amylopectin, which makes it possible to be widely applied to improve hydrolysis effect of amylase, increase the utilization rate of starch, improve quality of the product, decrease the grain consumption, and develop the new product in the processing industries with a good market prospect.

At present, the main problem limiting the industrial application of pullulanase is the low fermentation activity and high production cost of pullulanase producing strains. Expressing pullulanase in the heterogeneous host is an effective method to improve the enzyme activity of the fermentation produced pullulanase. Compared with the expression system of *E. coli* and *Pichia pastoris*, *Bacillus subtilis* is a food-grade expression system having strong ability to secrete protein, good fermentation basis and production technology. At present, many researchers try to express pullulanase in *Bacillus subtilis*, but the activity of the expressed enzyme is low. It has been found that the expression of pullulanase was affected by the following factors: (1) that *Bacillus subtilis* secretes a large number of proteases decomposing the pullulanase; (2) that no suitable promoter and signal peptide were found; and (3) that the expression plasmids may lose with the increase of passage times. Therefore, in order to improve the expression of pullulanase in *Bacillus subtilis*, the problems mentioned above must be solved.

Order of the Invention

According to the present invention, gene knockout technology is applied to *Bacillus subtilis* to obtain mutant *Bacillus subtilis* strain Bs-vtr with deletion of alkaline protease gene and neutral protease gene, which is transformed by the expression vector with the adaptively optimized combination of promoter and signal peptide, so as to efficiently express pullulanase, which is the basis of industrial application.

One order of the present invention is to reduce the influence of subtilisin on recombinant pullulanase by deleting alkaline protease gene and neutral protease gene, and transforming the mutant strain by the recombinant vector with optimized combination of promoter and signal peptide, so as to efficiently express pullulanase.

SUMMARY OF THE INVENTION

One aspect of the present invention is to provide a method for efficiently expressing pullulanase in *Bacillus subtilis* including the steps of constructing mutant *Bacillus subtilis* strain with deletion of alkaline protease gene and neutral protease gene, constructing expression vector including optimized combination of promoter and signal peptide and pullulanase gene, and transforming said mutant *Bacillus subtilis* strain with deletion of alkaline protease gene and neutral protease gene by said expression vector, wherein said promoter is selected from promoter of thermophilic α-amylase gene in *Bacillus licheniformis*, promoter of alkaline protease gene in *Bacillus subtilis*, promoter of neutral protease gene in *Bacillus subtilis*, promoter of medium temperature α-amylase gene in *Bacillus subtilis*, promoter of medium temperature α-Amylase gene in *Bacillus amyloliquefaciens*, and/or promoter from *Bacillus thuringiensis*, said signal peptide is selected from the signal peptide of thermophilic α-amylase in *Bacillus licheniformis*, the signal peptide of alkaline protease in *Bacillus subtilis* the signal peptide of neutral protease in *Bacillus subtilis*, the signal peptide of medium temperature α-amylase in *Bacillus subtilis*, the signal peptide of the medium temperature α-amylase in *Bacillus amyloliquefaciens*, and/or the signal peptide of chitinase in *Bacillus licheniformis*.

According to the method for efficiently expressing pullulanase in *Bacillus subtilis* of the present invention, preferably, said promoter is the promoter of alkaline protease gene in *Bacillus subtilis*, and said signal peptide is the signal peptide of medium temperature α-amylase in *Bacillus subtilis*.

According to an embodiment of the present invention, the method for efficiently expressing pullulanase in *Bacillus subtilis* includes the steps of constructing a mutant *Bacillus subtilis* strain with deletion of alkaline protease gene and neutral protease gene, constructing an expression vector including an optimized combination of promoter and signal peptide, and pullulanase gene, and transforming said mutant *Bacillus subtilis* strain with deletion of alkaline protease gene and neutral protease gene with said expression vector to express and isolate pullulanase, wherein said promoter is one or more hybrid promoters having the nucleotide sequence as set in forth in SEQ ID NO.14, SEQ ID NO.15, SEQ ID NO.16 and SEQ ID NO.17 respectively, and said signal peptide is selected from the signal peptide of thermophilic α-amylase in *Bacillus licheniformis*, the signal peptide of alkaline protease in *Bacillus subtilis*, the signal peptide of neutral protease in *Bacillus subtilis*, the signal peptide of medium temperature α-amylase in *Bacillus subtilis*, the signal peptide of the medium temperature α-amylase in *Bacillus amyloliquefaciens*, and/or the signal peptide of chitinase in *Bacillus licheniformis*.

Another aspect of the invention is to provide a recombinant *Bacillus subtilis* efficiently expressing pullulanase comprising a combination of promoter and signal peptide and pullulanase gene, with deletion of alkaline protease gene and neutral protease gene, wherein said promoter is selected from promoter of thermophilic α-amylase gene in *Bacillus licheniformis*, promoter of alkaline protease gene in *Bacillus subtilis* promoter of neutral protease gene in *Bacillus subtilis*, promoter of medium temperature α-amylase gene in *Bacillus subtilis*, promoter of medium temperature α-Amylase gene in *Bacillus amyloliquefaciens*, and/or promoter from *Bacillus thuringiensis*, said signal peptide is selected from the signal peptide of thermophilic α-amylase in *Bacillus licheniformis* the signal peptide of alkaline protease in *Bacillus subtilis*, the signal peptide of neutral protease in *Bacillus subtilis*, the signal peptide of medium temperature α-amylase in *Bacillus sub-* tilis, the signal peptide of the medium temperature α-amylase in *Bacillus amyloliquefaciens*, and/or the signal peptide of chitinase in *Bacillus licheniformis*.

According to an embodiment of the present invention, said recombinant *Bacillus subtilis* efficiently expressing pullulanase comprises a combination of a promoter and a signal peptide, and pullulanase gene, being deleted alkaline protease gene and neutral protease gene, wherein said promoter is one or more hybrid promoters having the nucleotide sequence as set in forth in SEQ ID NO.14, SEQ ID NO.15, SEQ ID NO.16 and SEQ ID NO.17 respectively, and said signal peptide is selected from the signal peptide of thermophilic α-amylase in *Bacillus licheniformis*, the signal peptide of alkaline protease in *Bacillus subtilis*, the signal peptide of neutral protease in *Bacillus subtilis*, the signal peptide of medium temperature α-amylase in *Bacillus subtilis*, the signal peptide of the medium temperature α-amylase in *Bacillus amyloliquefaciens*, and/or the signal peptide of chitinase in *Bacillus licheniformis*.

According to an embodiment of the present invention, alkaline protease gene and neutral protease gene are knocked out from *Bacillus subtilis*, to obtain a mutant *Bacillus subtilis* strain Bs-vtr for optimizing the combination of the promoter and signal peptide efficiently expressing pullulanase by taking pullulanase gene Bdp having the nucleotide sequence as set in forth in SEQ ID NO.1 as reporter gene, and combination of promoter P43 and signal peptide SacB as control, wherein said promoter is selected from promoter of thermophilic α-amylase gene in *Bacillus licheniformis* ($P_{bl}$), promoter of alkaline protease gene in *Bacillus subtilis* ($P_{ap}$), promoter of neutral protease gene in *Bacillus subtilis* ($P_{np}$), promoter of medium temperature α-amylase gene in *Bacillus subtilis* ($P_{ma}$), promoter of medium temperature α-Amylase gene in *Bacillus amyloliquefaciens* ($P_{ba}$), and/or promoter from *Bacillus thuringiensis* ($P_{bt}$), with the nucleotide sequence as set in forth in SEQ ID NO.2 to SEQ ID NO.7 respectively, and said signal peptide is selected from the signal peptide of thermophilic α-amylase in *Bacillus licheniformis*($S_{bl}$), the signal peptide of alkaline protease in *Bacillus subtilis*($S_{ap}$), the signal peptide of neutral protease in *Bacillus subtilis* ($S_{np}$), the signal peptide of medium temperature α-amylase in *Bacillus subtilis* ($S_{ma}$), the signal peptide of the medium temperature α-amylase in *Bacillus amyloliquefaciens* ($S_{ba}$), and/or the signal peptide of chitinase in *Bacillus licheniformis*. ($S_e$), having the amino sequence as set in forth in SEQ ID NO.8 to SEQ ID NO.13 respectively. Table 1 lists the recombinant *Bacillus subtilis* strains with the combinations of these promoters and signal peptides having 150% to 300% of the relative enzyme activity of the control.

Additionally, hybrid promoters with the nucleotide sequence as set in forth in SEQ ID NO.14 to SEQ ID NO.17 respectively are constructed based on the promoter of thermophilic α-amylase gene in *Bacillus licheniformis*, the promoter of alkaline protease gene in *Bacillus subtilis*, the promoter of neutral protease gene in *Bacillus subtilis*, the promoter of medium temperature α-amylase gene in *Bacillus subtilis*, the promoter of medium temperature α-Amylase gene in *Bacillus amyloliquefaciens*, and/or the promoter from *Bacillus thuringiensis*, in order to further improve the expression activity of pullulanase. Table 2 lists the hybrid promoters having the relative expression activity which is 400% to 700% of that of the control.

The present invention provides an application basis of pullulanase to industry by knocking out alkaline protease gene and neutral protease gene from *Bacillus subtilis*, optimizing combinations of promoters and signal peptides capable of efficiently expressing pullulanase.

EMBODIMENT

The present invention is further illustrated with reference to the following Examples and the appended drawings, which should by no means be construed as limitations of the present invention.

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Figure 1:
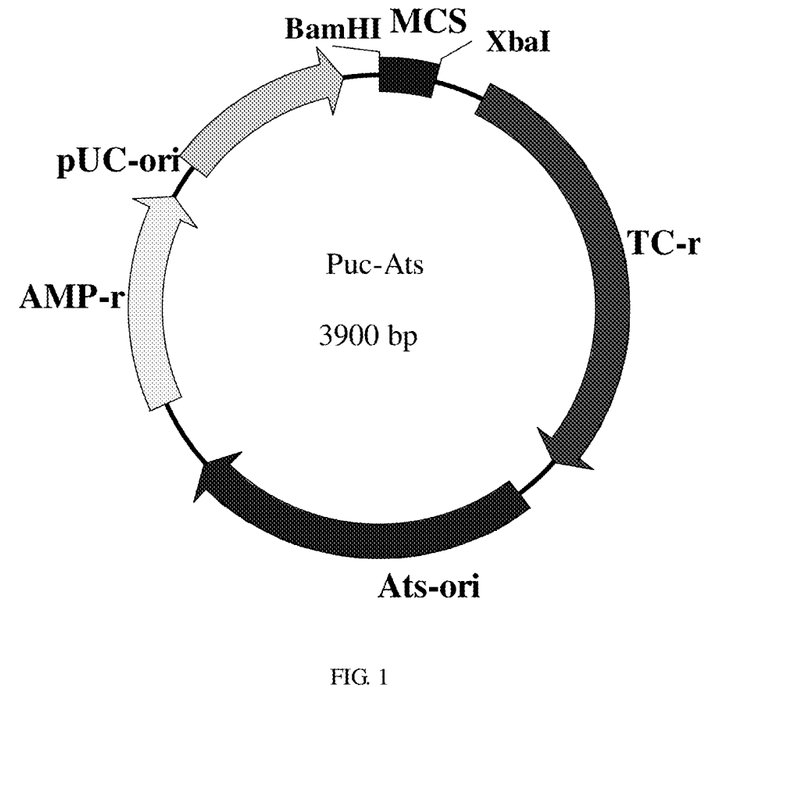
FIG. 1 is a schematic diagram of construct of knock-out vector Puc-Ats.
Figure 2:
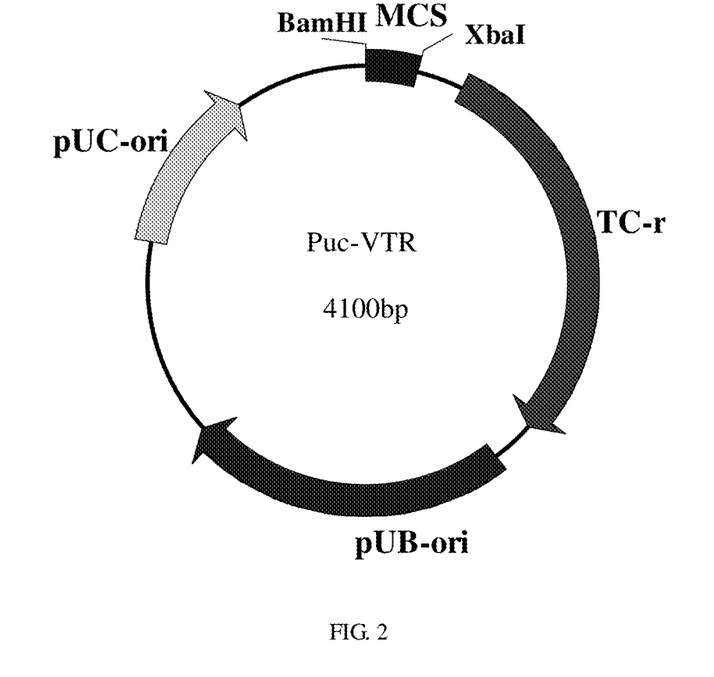
FIG. 2 is a schematic diagram of construct of expression vector Puc-vtr.

Test Materials and Reagents:

1. Strains and Vectors:

*Escherichia coli*. Top10, *Bacillus subtilis* 10033, *Bacillus licheniformis* 10037, *Bacillus amylolytic* 10079, *Bacillus thuringiensis* 20557 were purchased from China Center of Industrial Culture Collection (CICC). The maps of structures of the knockout vector puc-ats and expression vector puc-vtr are shown in FIG. 1 and FIG. 2.

2. Enzymes and Other Biochemical Reagents:

Q5 High-Fidelity DNA Polymerase (NEB), Plasmid extraction Kit, Agarose Gel DNA Purification Kit, and restriction enzyme were commercially available.

3. Medium:

*E. coli*. LB medium: 1% of peptone, 0.5% of yeast extract, and 1% of NaCl, natural pH.

Example 1 Constructing a *Bacillus subtilis* Strain with Deletion of Alkaline Protease Gene

*Bacillus subtilis* 10033 was inoculated into LB medium and cultured at 37° C. for 24 h for being extracted genomic DNA. The upper and lower homologous arms of the alkaline protease gene were amplified respectively, and then were fused by overlapping PCR. Finally, the PCR products were digested by the restriction enzymes BamHI and XbaI, purified, recovered, and then inserted into the vector Puc-Ats, followed by being transformed into *Escherichia coli* top10, in order to obtain an alkaline protease gene Knockout vector Puc-Ats-AprE.

*Bacillus subtilis* 10033 was eletro-transformed by Knockout vector Puc-Ats-AprE, and screened on tetracycline-resistant plates. The transformants growing on the tetracycline-resistant plates were induced at 45° C. to inactivate the replicator of the vector Puc-Ats-AprE, and promote the homologous recombination between the vector Puc-Ats-Apre and *Bacillus subtilis* 10033. 5'-terminal homologous arm and 3'-terminal homologous arm were amplified by PCR to determine the location of homologous arm single exchange.

The transformants for which the location of homologous single exchange has been determined were antibiotic-freely cultured and passaged for 10 times continuously, to screen the positive transformants with deletion of alkaline protease gene which growed on the antibiotic-free plates, but not on the antibiotic plates. The obtained positive transformants were identified by PCR, so as to obtain *Bacillus subtilis* strain with deletion of alkaline protease gene, named as Bs-1.

Example 2 Constructing *Bacillus subtilis* Strain with Deletion of Neutral Protease Gene The neutral protease gene was knocked out with the same method as in Example 1 taking Bs-1 as the starting stain. 5'-terminal homologous arm and 3'-terminal homologous arm were amplified by PCR to construct Knockout vector of neutral protease gene, Puc-Ats-NprE, which was electro-transformed into Bs-1. The transformants were induced at 45° C. to obtain single-exchange *Bacillus subtilis*, followed by antibiotic-freely passaging to obtain double-exchange *Bacillus subtilis* which was identified by PCR to obtain *Bacillus subtilis* with deletion of alkaline protease gene and neutral protease gene, named as Bs-vtr.

Example 3 Optimizing Combination of Promoter and Signal Peptide for Expressing Pullulanase 1. Cloning Promoter and Signal Peptide Gene

*Bacillus subtilis* 10033, *Bacillus licheniformis* 10037, *Bacillus* amylolysis 10079 and *Bacillus thuringiensis* 20557 were respectively inoculated into LB medium for expanding culture, followed by collecting the culture by centrifuging for extracting genomic DNA. The promoters and signal peptides are amplified by PCR to obtain the sequence of the promoter of thermophilic α-amylase gene in *Bacillus licheniformis* ($P_{bl}$), the promoter of alkaline protease gene in *Bacillus subtilis* ($P_{ap}$), promoter of neutral protease gene in *Bacillus subtilis* ($P_{np}$), the promoter of medium temperature α-amylase gene in *Bacillus subtilis* ($P_{ma}$), the promoter of medium temperature α-Amylase gene in *Bacillus amyloliquefaciens* ($P_{ba}$), and the promoter from *Bacillus thuringiensis* ($P_{bt}$), having the nucleotide sequence as set in forth in SEQ ID NO.2 to SEQ ID NO.7 respectively, and sequence of the signal peptide of thermophilic α-amylase in *Bacillus licheniformis* ($S_{bl}$), the signal peptide of alkaline protease in *Bacillus subtilis* ($S_{ap}$), the signal peptide of neutral protease in *Bacillus subtilis* ($S_{np}$), the signal peptide of medium temperature α-amylase in *Bacillus subtilis* ($S_{ma}$), the signal peptide of the medium temperature α-amylase in *Bacillus amyloliquefaciens* ($S_{ba}$), and the signal peptide of chitinase in *Bacillus licheniformis*. ($S_c$), having the amino sequence as set in forth in SEQ ID NO.8 to SEQ ID NO.13 respectively.

2. Combination of Promoter and Signal Peptide

The different promoters, the signal peptides and pullulanase Bdp gene were fused together by overlapping PCR, followed by being inserted into the expression vector Puc-vtr to obtain the desired expression vector of pullulanase gene, for electro-transforming the host, Bs-vtr. The transformants were cultured in the enzyme-producing medium for 24 h, followed by detecting the enzyme activity according to national standard GB 1886.174-2016.

The efficient combinations of the promoter and the signal peptide were selected according to the relative activity of pullulanase with respect to a series of combinations of the different promoters and the different signal peptides as list in Table 1. As showed in Table 1, the relative activity of pullulanase for all of the optimized combinations of the promoter and the signal peptides was improved compared to that of the control combination, wherein the highest relative enzyme activity, being 300%, was detected in the combination of the promoter of alkaline protease gene in *Bacillus subtilis* and the signal peptide of medium temperature α-amylase in *Bacillus subtilis*, and the second highest relative enzyme activity, being 210%, was detected in the combination of the promoter of medium temperature α-Amylase gene in *Bacillus subtilis* and the signal peptide of neutral protease in *Bacillus subtilis*.

TABLE 1

| Combination of promoter and signal peptide | The relative activity of the expressed pullulanase (%) |
|---|---|
| Control: P43 + SacB | 100 |
| $P_{ap} + S_{ma}$ | 300 |
| $P_{ap} + S_{bl}$ | 225 |
| $P_{ap} + S_{np}$ | 178 |
| $P_{ma} + S_{np}$ | 210 |
| $P_{ba} + S_c$ | 198 |
| $P_{ma} + S_{ap}$ | 168 |
| $P_{bl} + S_{ba}$ | 190 |
| $P_{bl} + S_c$ | 180 |
| $P_{np} + S_{bl}$ | 160 |
| $P_{np} + S_{ma}$ | 189 |
| $P_{ma} + S_{ap}$ | 175 |
| $P_{ma} + S_{bl}$ | 180 |
| $P_{bt} + S_{bl}$ | 169 |
| $P_{bt} + S_{ap}$ | 186 |

In Table 1, "$P_{bl}$" represents promoter of thermophilic α-amylase gene in *bacillus licheniformis*, "$P_{ap}$" represents promoter of alkaline protease gene in *bacillus subtilis*, "$P_{np}$" represents promoter of neutral protease gene in *bacillus subtilis*, "$P_{ma}$" represents promoter of medium temperature α-amylase gene in *bacillus subtilis*, "$P_{ba}$" represents promoter of medium temperature α-Amylase gene in *bacillus amyloliquefaciens*, "$P_{bt}$" represents promoter from *bacillus thuringiensis*, "$S_{bl}$"represents signal peptide of thermophilic α-amylase in *bacillus licheniformis*, "$S_{ap}$" represents the signal peptide of alkaline protease in *bacillus subtilis*, "$S_{np}$" represents the signal peptide of neutral protease in *bacillus subtilis*, "$S_{ma}$" represents the signal peptide of medium temperature α-amylase in *bacillus subtilis*, "$S_{ba}$" represents the signal peptide of the medium temperature α-amylase in *bacillus amyloliquefaciens*, and "$S_c$" presents signal peptide of chitinase in *bacillus licheniformis*.

Example 4 Constructing Hybrid Promoter

One or more promoter selected from the group of $P_{bl}$, $P_{ap}$, $P_{np}$, $P_{ma}$, $P_{ba}$ and $P_{bt}$ were combined, and were further combined with different signal peptides selected from the group of $S_{bl}$, $S_{ap}$, $S_{np}$, $S_{ma}$, $S_{ba}$ or $S_c$. Four hybrid promoters efficiently expressing pullulanase were selected, named as promoter P 1, P 2, P 3 and P 4, with the nucleotides sequence as set in forth in SEQ ID NO.14 to SEQ ID NO.17 respectively, wherein the promoter P1 consists of $P_{bl}$, $P_{ap}$ and $P_{ba}$, the promoter P2 consists of $P_{bl}$, $P_{ba}$ and $P_{bt}$, the promoter P3 consists of $P_{bl}$, $P_{np}$ and $P_{bt}$, and the promoter P 4 consists of $P_{ap}$, $P_{ba}$ and $P_{np}$. The table 2 lists the relative activity of expressed pullulanase for the combinations of the above four hybrid promoters and the signal peptides selected from $S_{bl}$, $S_{ap}$, $S_{np}$, $S_{ma}$, $S_{ba}$ or $S_c$.

TABLE 2

| Combination of promoter and singal peptide | The relative activity of the expressed pullulanase (%) |
|---|---|
| Control: P43 + SacB | 100 |
| $P_1 + S_{ma}$ | 400 |
| $P_1 + S_{bl}$ | 620 |
| $P_1 + S_{np}$ | 580 |
| $P_1 + S_{ba}$ | 450 |
| $P_1 + S_c$ | 620 |
| $P_2 + S_{ap}$ | 480 |
| $P_2 + S_{ba}$ | 450 |
| $P_2 + S_c$ | 470 |
| $P_2 + S_{bl}$ | 490 |
| $P_2 + S_{ma}$ | 430 |
| $P_3 + S_{ap}$ | 560 |
| $P_3 + S_{bl}$ | 550 |
| $P_3 + S_c$ | 630 |
| $P_3 + S_{ba}$ | 650 |

TABLE 2-continued

| Combination of promoter and singal peptide | The relative activity of the expressed pullanase (%) |
|---|---|
| $P_3 + S_{ma}$ | 590 |
| $P_4 + S_c$ | 600 |
| $P_4 + S_{ap}$ | 580 |
| $P_4 + S_{ba}$ | 610 |
| $P_4 + S_{ma}$ | 570 |
| $P_4 + S_{bl}$ | 620 |

Example 5 Constructing Pullulanase-Integrated *Bacillus subtilis*

The combinations of promoters and signal peptides obtained in the examples 3 and 4, pullulanase gene, and the part of the medium temperature α-amylase gene as the homologous arm were integrated into the Knock-out integrating vector Puc-Ats, taking the medium temperatures-amylase gene as the target integration site, to obtain the corresponding Knock-out integrating vector, followed by constructing pullulanase-integrated *Bacillus subtilis* by the same method as described in Example 1, as so to obtain the corresponding pullulanase-integrated *Bacillus subtilis*.

The invention claimed is:

1. A method for efficiently expressing pullulanase in *Bacillus subtilis* comprising the steps of constructing *Bacillus subtilis* strain with deletion of alkaline protease gene and neutral protease gene, constructing expression vector including a combination of promoter and signal peptide and pullulanase gene, and transforming said *Bacillus subtilis* strain with deletion of alkaline protease gene and neutral protease gene by said expression vector, wherein said promoter is a hybrid promoter having the nucleotide sequence of SEQ ID NO:14, SEQ ID NO:15, SEQ ID NO:16 or SEQ ID NO.17, respectively, and said signal peptide has the nucleotide sequence of SEQ ID NO: 8, SEQ ID NO: 9, SEQ ID NO:10, SEQ ID NO:11, SEQ ID NO:12 or SEQ ID NO:13.

2. A recombinant *Bacillus subtilis* efficiently expressing pullulanase, comprising a combination of promoter and signal peptide for expressing pullulanase, and pullulanase gene, and having deletion of alkaline protease gene and neutral protease gene, wherein said promoter is a hybrid promoter having the nucleotide sequence of SEQ ID NO:14, SEQ ID NO:15, SEQ ID NO:16 or SEQ ID NO.17, respectively; and said signal peptide has the nucleotide sequence of SEQ ID NO:8, SEQ ID NO:9, SEQ ID NO:10, SEQ ID NO:11, SEQ ID NO:12 or SEQ ID NO:13.

* * * * *

SEQUENCE LISTING

```
<160> NUMBER OF SEQ ID NOS: 17

<210> SEQ ID NO 1
<211> LENGTH: 2493
<212> TYPE: DNA
<213> ORGANISM: Artificial Sequence
<220> FEATURE:
<223> OTHER INFORMATION: Gene

<400> SEQUENCE: 1
gaaaaagatg ctgaggatgc agctaaaccc gctgtaagca acgcttattt agatgcttca      60
aaccaggtgc tggttaaact tagccagccg ttaactcttg gggaaggcgc aagcggcttt     120
acggttcatg acgacacagc aaataaggat attccagtga catctgtgaa ggatgcaagt     180
cttggtcaag atgtaaccgc tgttttggca ggtaccttcc aacatatttt tggaggttcc     240
gattgggcac ctgataatca cagtacttta ttaaaaaagg tgactaacaa tctctatcaa     300
ttctcaggag atcttcctga aggaaactac caatataaag tggctttaaa tgatagctgg     360
aataatccga gttacccatc tgacaacatt aatttaacag tccctgccgg cggtgcacac     420 gtcactttt cgtatattcc gtccactcat gcagtctatg acacaattaa taatcctaat     480
gcggatttac aagtagaaag cggggttaaa acggatctcg tgacggttac tctaggggaa     540
gatccagatg tgagccatac tctgtccatt caaacagatg ctatcaggc aaagcaggtg      600 atacctcgta atgtgcttaa ttcatcacag tactactatt caggagatga tcttgggaat     660
acctatacac agaaagcaac aacctttaaa gtctgggcac caacttctac tcaagtaaat     720
gttcttcttt atgacagtgc aacgggttct gtaacaaaaa tcgtacctat gacggcatcg     780
ggccatggtg tgtgggaagc aacggttaat caaaaccttg aaaattggta ttacatgtat     840
gaggtaacag gccaaggctc tacccgaacg gctgttgatc cttatgcaac tgcgattgca     900
ccaaatggaa cgagaggcat gattgtggac ctggctaaaa cagatcctgc tggctggaac     960
agtgataaac atattacgcc aaagaatata gaagatgagg tcatctatga aatggatgtc    1020
cgtgactttt ccattgaccc taattcgggt atgaaaaata aagggaagta tttggctctt    1080
acagaaaaag gaacaaaggg ccctgacaac gtaaagacgg ggatagattc cttaaaacaa    1140
cttgggatta ctcatgttca gcttatgcct gttttcgcat ctaacagtgt cgatgaaact    1200
gatccaaccc aagataattg gggttatgac cctcgcaact atgatgttcc tgaagggcag    1260
tatgctacaa atgcgaatgg taatgctcgt ataaaagagt ttaaggaaat ggttctttca    1320
ctccatcgta aacacattgg ggttaacatg gatgttgtct ataatcatac ctttgccacg    1380
caaatctctg acttcgataa aattgtacca gaatattatt accgtacgga tgatgcaggt    1440
aattatacca acggatcagg tactggaaat gaaattgcag ccgaaaggcc aatggttcaa    1500
aaatttatta ttgattccct taagtattgg gtcaatgagt atcatattga cggcttccgt    1560
```

```
tttgacttaa tggcgctgct tggaaaagac acgatgtcca aagctgcctc ggagcttcat    1620
gctattaatc caggaattgc actttacggt gagccatgga cgggtggaac ctctgcactg    1680
ccagatgatc agcttctgac aaaaggagct caaaaaggca tgggagtagc ggtgtttaat    1740
gacaatttac gaaacgcgtt ggacggcaat gtctttgatt cttccgctca aggttttgcg    1800
acaggtgcaa caggcttaac tgatgcaatt aagaatggcg ttgaggggag tattaatgac    1860
tttacctctt caccaggtga gacaattaac tatgtcacaa gtcatgataa ctacacccct    1920
tgggacaaaa tagccctaag caatcctaat gattccgaag cggatcggat taaaatggat    1980
gaactcgcac aagcagttgt tatgacctca caaggcgttc cattcatgca aggcggggaa    2040
gaaatgcttc gtacaaaagg cggcaacgac aatagttata atgcaggcga tgcggtcaat    2100
gagtttgatt ggagcaggaa agctcaatat ccagatgttt tcaactatta tagcgggcta    2160
atccaccttc gtcttgatca cccagccttc cgcatgacga cagctaatga aatcaatagc    2220
cacctccaat tcctaaatag tccagagaac acagtggcct atgaattaac tgatcatgtt    2280
aataaagaca aatggggaaa tatcattgtt gtttataacc caaataaaac tgtagcaacc    2340
atcaatttgc cgagcgggaa atgggcaatc aatgctacga gcgtaaggt aggagaatcc     2400 acccttggtc aagcagaggg aagtgtccaa gtaccaggta tatctatgat gatccttcat    2460
caagaggtaa gcccagacca cggtaaaaag taa                                 2493

<210> SEQ ID NO 2
<211> LENGTH: 607
<212> TYPE: DNA
<213> ORGANISM: Artificial Sequence
<220> FEATURE:
<223> OTHER INFORMATION: Promoter

<400> SEQUENCE: 2
ccttctttgt gcttggaagc agagcccaat attatcccga aacgataaaa cggatgctga     60
aggaaggaaa cgaagtcggc aaccattcct gggaccatcc gttattgaca aggctgtcaa    120
acgaaaaagc gtatcaggag attaacgaca cgcaagaaat gatcgaaaaa atcagcggac    180
acctgcctgt acacttgcgt cctccatacg gcgggatcaa tgattccgtc cgctcgcttt    240
ccaatctgaa ggtttcattg tgggatgttg atccggaaga ttggaagtac aaaaataagc    300
aaaagattgt caatcatgtc atgagccatg cgggagacgg aaaaatcgtc ttaatgcacg    360
atatttatgc aacgtccgca gatgctgctg aagagattat taaaaagctg aaagcaaaag    420
gctatcaatt ggtaactgta tctcagcttg aagaagtgaa gaagcagaga ggctattgaa    480
taaatgagta gaaagcgcca tatcggcgct tttctttttgg aagaaaatat agggaaaatg    540
gtatttgtta aaaattcgga atatttatac aatatcatat gtttcacatt gaaagggag    600 gagaatc                                                              607

<210> SEQ ID NO 3
<211> LENGTH: 191
<212> TYPE: DNA
<213> ORGANISM: Artificial Sequence
<220> FEATURE:
<223> OTHER INFORMATION: Promoter

<400> SEQUENCE: 3
gttcttttct gtatgaaaat agttatttcg agtctctacg gaaatagcga gagatgatat     60
acctaaatag agataaaatc atctcaaaaa aatgggtcta ctaaaatatt attccatcta    120
```

| ttacaataaa ttcacagaat agtcttttaa gtaagtctac tctgaactta agcaaaagga | 180 |
| gagggacgcg t | 191 |

<210> SEQ ID NO 4
<211> LENGTH: 361
<212> TYPE: DNA
<213> ORGANISM: Artificial Sequence
<220> FEATURE:
<223> OTHER INFORMATION: Promoter

<400> SEQUENCE: 4

| cctttacttc ttattaaggc ctcattcggt tagacagcgg actttt caaa aagtttcaag | 60 |
| atgaaacaaa aatatctcat cttcccct tg atatgtaaaa aacataactc ttgaatgaac | 120 |
| caccacatga cacttgactc atcttgatat tattcaacaa aaacaaacac aggacaatac | 180 |
| tatcaatttt gtctagttat gtacatgaca cttgactcat cttgatatta ttcaacaaaa | 240 |
| acaaacacag gacaatacta tcaattttgt ctagttatgt tagttt ttgt tgagtattcc | 300 |
| agaatgctag tttaatataa caatataaag ttttcagtat tttcaaaaag ggggatttat | 360 |
| t | 361 |

<210> SEQ ID NO 5
<211> LENGTH: 380
<212> TYPE: DNA
<213> ORGANISM: Artificial Sequence
<220> FEATURE:
<223> OTHER INFORMATION: Promoter

<400> SEQUENCE: 5

| ggctgaaaat gattcttctt tttatcgtct gcggcggcgt tctgtttctg cttcggtatg | 60 |
| tgattgtgaa gctggcttac agaagagcgg taaaagaaga aataaaaaag aaatcatctt | 120 |
| gaaaaataga tggtttcttt ttttgtttgg aaagcgaggg aagcgttcac agtttcgggc | 180 |
| agctttttt ataggaacat tgatttgtat tcactctgcc aagttgtttt gatagagtga | 240 |
| ttgtgataat tttaaatgta agcgttaaca aaattctcca gtcttcacat cggtttgaaa | 300 |
| ggaggaagcg gaagaatgaa gtaagaggga tttttgactc cgaagtaagt cttcaaaaaa | 360 |
| tcaaataagg agtgtcaaga | 380 |

<210> SEQ ID NO 6
<211> LENGTH: 365
<212> TYPE: DNA
<213> ORGANISM: Artificial Sequence
<220> FEATURE:
<223> OTHER INFORMATION: Promoter

<400> SEQUENCE: 6

| cgcttctgaa acgcagctgg tcaactgtgt aagcaaggct gaacaaggca gcgtatatat | 60 |
| gccgaagatc atccgcaaag ggcgcattca agtatcagta tcaacaagcg ggcaagccc | 120 |
| cgcacatacg aaaagactgg ctgaaaacat tgagcctttg atgactgatg atttggctga | 180 |
| agaagtggat cgattgtttg agaaaagaag aagaccataa aaatacctttg tctgtcatca | 240 |
| gacagggtat ttttatgct gtccagactg tccgctgtgt aaaaaatagg aataaagggg | 300 |
| ggttgttatt attttactga tatgtaaaat ataatttgta taagaaaatg agagggagag | 360 |
| gaaac | 365 |

<210> SEQ ID NO 7
<211> LENGTH: 619

```
<212> TYPE: DNA
<213> ORGANISM: Artificial Sequence
<220> FEATURE:
<223> OTHER INFORMATION: Promoter

<400> SEQUENCE: 7
tcgaaacgta agatgaaacc ttagataaaa gtgcttttt  tgttgcaatt gaagaattat    60
taatgttaag cttaattaaa gataatatct ttgaattgta acgcccctca aaagtaagaa   120
ctacaaaaaa agaatacgtt atatagaaat atgtttgaac cttcttcaga ttacaaatat   180
attcggacgg actctacctc aaatgcttat ctaactatag aatgacatac aagcacaacc   240
ttgaaaattt gaaaatataa ctaccaatga acttgttcat gtgaattatc gctttattta   300
attttctcaa ttcaatatat aatatgccaa tacattgtta caagtagaaa ttaagacacc   360
cttgatagcc ttactatacc taacatgatg tagtattaaa tgaatatgta aatatattta   420
tgataagaag cgacttattt ataatcatta catattttc tattggaatg attaagattc    480
caatagaata gtgtataaat tatttatctt gaaaggaggg atgcctaaaa acgaagaaca   540
ttaaaaacat atatttgcac cgtctaatgg atttatgaaa aatcatttta tcagtttgaa   600
aattatgtat tatgaaaag                                                619

<210> SEQ ID NO 8
<211> LENGTH: 87
<212> TYPE: DNA
<213> ORGANISM: Artificial Sequence
<220> FEATURE:
<223> OTHER INFORMATION: Promoter

<400> SEQUENCE: 8
atgaaacaac aaaaacggct ttacgcccga ttgctgacgc tgttatttgc gctcatcttc    60
ttgctgcctc attctgcagc agcggcg                                        87

<210> SEQ ID NO 9
<211> LENGTH: 87
<212> TYPE: DNA
<213> ORGANISM: Artificial Sequence
<220> FEATURE:
<223> OTHER INFORMATION: Promoter

<400> SEQUENCE: 9
gtgagaagca aaaaattgtg gatcagcttg ttgtttgcgt taacgttaat ctttacgatg    60
gcgttcagca acatgtctgc gcaggct                                        87

<210> SEQ ID NO 10
<211> LENGTH: 81
<212> TYPE: DNA
<213> ORGANISM: Artificial Sequence
<220> FEATURE:
<223> OTHER INFORMATION: Promoter

<400> SEQUENCE: 10
gtgggtttag gtaagaaatt gtctgttgct gtcgctgctt cgtttatgag tttatcaatc    60
agcctgccag gtgttcaggc t                                              81

<210> SEQ ID NO 11
<211> LENGTH: 99
<212> TYPE: DNA
<213> ORGANISM: Artificial Sequence
<220> FEATURE:
<223> OTHER INFORMATION: Promoter
```

<400> SEQUENCE: 11

```
atgtttgcaa acgattcaa aacctcttta ctgccgttat tcgctggatt tttattgctg    60
tttcatttgg ttctggcagg accggcggct gcgagtgct                          99
```

<210> SEQ ID NO 12
<211> LENGTH: 93
<212> TYPE: DNA
<213> ORGANISM: Artificial Sequence
<220> FEATURE:
<223> OTHER INFORMATION: Promoter

<400> SEQUENCE: 12

```
atgattcaaa acgaaagcg acagtttcg ttcagacttg tgcttatgtg cacgctgtta    60
tttgtcagtt tgccgattac aaaaacatca gcc                                93
```

<210> SEQ ID NO 13
<211> LENGTH: 99
<212> TYPE: DNA
<213> ORGANISM: Artificial Sequence
<220> FEATURE:
<223> OTHER INFORMATION: Promoter

<400> SEQUENCE: 13

```
atgttgatca acaaaagcaa aaagttttc gttttttctt tcatttttgt tatgatgctg    60
agcctctcat tgtgaatgg ggaagttgca aaagccgca                           99
```

<210> SEQ ID NO 14
<211> LENGTH: 1163
<212> TYPE: DNA
<213> ORGANISM: Artificial Sequence
<220> FEATURE:
<223> OTHER INFORMATION: Promoter

<400> SEQUENCE: 14

```
ccttctttgt gcttggaagc agagcccaat attatcccga acgataaaa cggatgctga    60
aggaaggaaa cgaagtcggc aaccattcct gggaccatcc gttattgaca aggctgtcaa   120
acgaaaaagc gtatcaggag attaacgaca cgcaagaaat gatcgaaaaa atcagcggac   180
acctgcctgt acacttgcgt cctccatacg gcgggatcaa tgattccgtc cgctcgcttt   240
ccaatctgaa ggtttcattg tgggatgttg atccggaaga ttggaagtac aaaaataagc   300
aaaagattgt caatcatgtc atgagccatg cgggagacgg aaaaatcgtc ttaatgcacg   360
atatttatgc aacgtccgca gatgctgctg aagagattat taaaaagctg aaagcaaaag   420
gctatcaatt ggtaactgta tctcagcttg aagaagtgaa gaagcagaga ggctattgaa   480
taaatgagta gaaagcgcca tatcggcgct tttcttttgg aagaaaatat agggaaaatg   540
gtatttgtta aaaattcgga atatttatac aatatcatat gtttcacatt gaaagggag    600
gagaatcgtt cttttctgta tgaaaatagt tatttcgagt ctctacggaa atagcgagag   660
atgatatacc taaatagaga taaatcatc tcaaaaaaat gggtctacta aaatattatt    720
ccatctatta caataaattc acagaatagt cttttaagta agtctactct gaacttaagc   780
aaaaggagag ggacgcgtcg cttctgaaac gcagctggtc aactgtgtaa gcaaggctga   840
acaaggcagc gtatatatgc cgaagatcat ccgcaaaggg cgcattcaag tatcagtatc   900
aacaagcggg gcaagcccg cacatacgaa aagactggct gaaaacattg agcctttgat    960
gactgatgat ttggctgaag aagtggatcg attgttgag aaagaagaa gaccataaaa   1020
ataccttgtc tgtcatcaga cagggtattt tttatgctgt ccagactgtc cgctgtgtaa   1080
```

```
aaaataggaa taaagggggg ttgttattat tttactgata tgtaaaatat aatttgtata      1140
agaaaatgag agggagagga aac                                              1163

<210> SEQ ID NO 15
<211> LENGTH: 1413
<212> TYPE: DNA
<213> ORGANISM: Artificial Sequence
<220> FEATURE:
<223> OTHER INFORMATION: Promoter

<400> SEQUENCE: 15
ccttctttgt gcttggaagc agagcccaat attatcccga aacgataaaa cggatgctga        60
aggaaggaaa cgaagtcggc aaccattcct gggaccatcc gttattgaca aggctgtcaa       120
acgaaaaagc gtatcaggag attaacgaca cgcaagaaat gatcgaaaaa atcagcggac       180
acctgcctgt acacttgcgt cctccatacg gcgggatcaa tgattccgtc cgctcgcttt       240
ccaatctgaa ggtttcattg tgggatgttg atccggaaga ttggaagtac aaaaataagc       300
aaaagattgt caatcatgtc atgagccatg cgggagacgg aaaaatcgtc ttaatgcacg       360
atatttatgc aacgttcgca gatgctgctg aagagattat taaaaagctg aaagcaaaag       420
gctatcaatt ggtaactgta tctcagcttg aagaagtgaa gaagcagaga ggctattgaa       480
taaatgagta gaagcgccat atcggcgctt ttcttttgga agaaaatata gggaaaatgg       540
tacttgttaa aaattcggaa tatttataca atatcatatg ttacacattg aaagggcctt       600
aagggcctgc aatcgattgt ttgagaaaag aagaagacca taaaaatacc ttgtctgtca       660
tcagacaggg tattttttat gctgtccaga ctgtccgctg tgtaaaaaa aggaataaag       720 gggggttgac attattttac tgatatgtat aatataattt gtaagaaaa atggagctct       780 cgaaacgtaa gatgaaacct tagataaaag tgctttttt gttgcaattg aagaattatt       840
aatgttaagc ttaattaaag ataatatctt tgaattgtaa cgcccctcaa agtaagaac       900 tacaaaaaaa gaatacgtta tatagaaata tgtttgaacc ttcttcagat tacaaatata       960
ttcggacgga ctctacctca aatgcttatc taactataga atgacataca agcacaacct      1020 tgaaaattg aaaatataac taccaatgaa cttgttcatg tgaattatcg ctttatttaa      1080
ttttctcaat tcaatatata atatgccaat acattgttac aagtagaaat taagacaccc      1140
ttgatagcct tactatacct aacatgatgt agtattaaat gaatatgtaa atatatttat      1200
gataagaagc gacttattta taatcattac atatttttct attggaatga ttaagattcc      1260
aatagaatag tgtataaatt atttatcttg aaaggaggga tgcctaaaaa cgaagaacat      1320
taaaaacata tatttgcacc gtctaatgga tttatgaaaa atcattttat cagtttgaaa      1380
attatgtatt atgaaaagtg aggagggaac cga                                  1413

<210> SEQ ID NO 16
<211> LENGTH: 1587
<212> TYPE: DNA
<213> ORGANISM: Artificial Sequence
<220> FEATURE:
<223> OTHER INFORMATION: Promoter

<400> SEQUENCE: 16
ccttctttgt gcttggaagc agagcccaat attatcccga aacgataaaa cggatgctga        60
aggaaggaaa cgaagtcggc aaccattcct gggaccatcc gttattgaca aggctgtcaa       120
acgaaaaagc gtatcaggag attaacgaca cgcaagaaat gatcgaaaaa atcagcggac       180
```

```
acctgcctgt acacttgcgt cctccatacg gcgggatcaa tgattccgtc cgctcgcttt      240
ccaatctgaa ggtttcattg tgggatgttg atccggaaga ttggaagtac aaaaataagc      300
aaaagattgt caatcatgtc atgagccatg cgggagacgg aaaaatcgtc ttaatgcacg      360
atatttatgc aacgtccgca gatgctgctg aagagattat aaaaagctg aaagcaaaag       420 gctatcaatt ggtaactgta tctcagcttg aagaagtgaa gaagcagaga ggctattgaa      480
taaatgagta gaaagcgcca tatcggcgct tttcttttgg aagaaaatat agggaaaatg      540
gtatttgtta aaaattcgga atatttatac aaatatcatat gtttcacatt gaaaggggag     600
gagaatccct ttacttctta ttaaggcctc attcggttag acagcggact tttcaaaaag      660
tttcaagatg aaacaaaaat atctcatctt ccccttgata tgtaaaaaac ataactcttg      720
aatgaaccac cacatgacac ttgactcatc ttgatattat tcaacaaaaa caaacacagg      780
acaatactat caattttgtc tagttatgta catgacactt gactcatctt gatattattc      840
aacaaaaaca aacacaggac aatactatca attttgtcta gttatgttag ttttgttga      900 gtattccaga atgctagttt aatataacaa tataaagttt tcagtatttt caaaaggggg      960
gatttatttc gaaacgtaag atgaaacctt agataaagt gctttttttg ttgcaattga      1020
agaattatta atgttaagct taattaaaga taatatcttt gaattgtaac gcccctcaaa     1080
agtaagaact acaaaaaaag aatacgttat atagaaatat gtttgaacct tcttcagatt     1140
acaaatatat tcggacggac tctacctcaa atgcttatct aactatagaa tgacatacaa     1200
gcacaacctt gaaaatttga aaatataact accaatgaac ttgttcatgt gaattatcgc     1260
tttatttaat tttctcaatt caatatataa atgccaata cattgttaca agtagaaatt      1320
aagacaccct tgatagcctt actataccta acatgatgta gtattaaatg aatatgtaaa     1380
tatatttatg ataagaagcg acttatttat aatcattaca tatttttcta ttggaatgat     1440
taagattcca atagaatagt gtataaatta tttatcttga aaggagggat gcctaaaaac     1500
gaagaacatt aaaaacatat atttgcaccg tctaatggat ttatgaaaaa tcattttatc     1560
agtttgaaaa ttatgtatta tgaaaag                                         1587
```

<210> SEQ ID NO 17
<211> LENGTH: 917
<212> TYPE: DNA
<213> ORGANISM: Artificial Sequence
<220> FEATURE:
<223> OTHER INFORMATION: Promoter

<400> SEQUENCE: 17

```
gttcttttct gtatgaaaat agttatttcg agtctctacg gaaatagcga gagatgatat       60
acctaaatag agataaaatc atctcaaaaa aatgggtcta ctaaaatatt attccatcta      120
ttacaataaa ttcacagaat agtctttttaa gtaagtctac tctgaactta agcaaaagga    180
gagggacgcg tcgcttctga aacgcagctg gtcaactgtg taagcaaggc tgaacaaggc     240
agcgtatata tgccgaagat catccgcaaa gggcgcattc aagtatcagt atcaacaagc    300
ggggcaagcc ccgcacatac gaaaagactg gctgaaaaca ttgagccttt gatgactgat     360
gatttggctg aagaagtgga tcgattgttt gagaaaagaa gaagaccata aaaataccct    420
gtctgtcatc agacagggta tttttatgc tgtccagact gtccgctgtg taaaaaatag    480
gaataaaggg gggttgttat tattttactg atatgtaaaa ataatttgt ataagaaaat      540 gagagggaga ggaaaccctt tacttcttat taaggcctca ttcggttaga cagcggactt     600
ttcaaaaagt ttcaagatga aacaaaaata tctcatcttc cccttgatat gtaaaaaaca    660
```

```
taactcttga atgaaccacc acatgacact tgactcatct tgatattatt caacaaaaac      720
aaacacagga caatactatc aattttgtct agttatgtac atgacacttg actcatcttg      780
atattattca acaaaaacaa acacaggaca atactatcaa ttttgtctag ttatgttagt      840
ttttgttgag tattccagaa tgctagttta atataacaat ataaagtttt cagtattttc      900
aaaaaggggg atttatt                                                    917
```